United States Patent
Muller et al.

(10) Patent No.: US 11,160,760 B2
(45) Date of Patent: Nov. 2, 2021

(54) SOFT CAPSULE BASED ON STARCH AND A METHOD AND DEVICE FOR THE PRODUCTION THEREOF

(71) Applicant: INNOGEL AG, Hunenberg (CH)

(72) Inventors: Rolf Muller, Zurich (CH); Federico Innerebner, Zurich (CH)

(73) Assignee: INNOGEL AG, Hunenberg (CH)

( * ) Notice: Subject to any disclaimer, the term of this patent is extended or adjusted under 35 U.S.C. 154(b) by 417 days.

(21) Appl. No.: 13/839,426

(22) Filed: Mar. 15, 2013

(65) Prior Publication Data
US 2013/0216618 A1    Aug. 22, 2013

Related U.S. Application Data

(63) Continuation of application No. 13/255,072, filed as application No. PCT/EP2010/052702 on Mar. 3, 2010, now Pat. No. 9,339,474.

(30) Foreign Application Priority Data

Mar. 3, 2009    (CH) .................................... 00324/09

(51) Int. Cl.
| | | |
|---|---|---|
| A61J 3/07 | (2006.01) | |
| C08L 3/00 | (2006.01) | |
| C08L 3/02 | (2006.01) | |
| C08L 3/04 | (2006.01) | |
| A61K 9/48 | (2006.01) | |
| B29C 43/00 | (2006.01) | |
| B29C 43/44 | (2006.01) | |
| B29C 43/48 | (2006.01) | |
| C08L 3/08 | (2006.01) | |

(52) U.S. Cl.
CPC ............ *A61K 9/4816* (2013.01); *A61J 3/077* (2013.01); *A61K 9/4833* (2013.01); *A61K 9/4866* (2013.01); *B29C 43/003* (2013.01); *B29C 43/44* (2013.01); *B29C 43/48* (2013.01); *C08L 3/00* (2013.01); *A61J 3/072* (2013.01); *A61J 3/074* (2013.01); *B29C 2043/486* (2013.01); *B29K 2003/00* (2013.01); *C08L 3/02* (2013.01); *C08L 3/04* (2013.01); *C08L 3/08* (2013.01)

(58) Field of Classification Search
CPC .. A61K 9/4816; A61K 9/4833; A61K 9/4866; A61J 3/077; A61J 3/072; A61J 3/074; B29C 43/44; B29C 43/48; B29C 2043/486; B29C 2003/00; C08L 3/00; C08L 3/02; C08L 3/04; C08L 3/08
USPC ...................................................... 514/778
See application file for complete search history.

(56) References Cited

U.S. PATENT DOCUMENTS

| | | |
|---|---|---|
| 3,098,492 A | 7/1963 | Wurtzburg et al. |
| 3,661,154 A | 5/1972 | Torr |
| 4,454,268 A | 6/1984 | Otey et al. |
| 5,342,626 A | 8/1994 | Winston, Jr. et al. |
| 5,342,646 A | 8/1994 | Kleese et al. |
| 5,409,973 A | 4/1995 | Bastioli et al. |
| 5,439,953 A | 8/1995 | Ritter et al. |
| 6,375,981 B1 | 4/2002 | Gilleland et al. |
| 6,489,386 B1 | 12/2002 | Plotzker et al. |
| 6,528,088 B1 | 3/2003 | Gilleland et al. |
| 6,770,293 B2 | 8/2004 | Angel et al. |
| 6,790,495 B1 | 9/2004 | Tomka et al. |
| 6,949,256 B2 | 9/2005 | Fonkwe et al. |
| 9,339,474 B2 | 5/2016 | Muller et al. |
| 9,486,415 B2 | 11/2016 | Muller et al. |
| 2003/0104048 A1 | 6/2003 | Patel et al. |
| 2003/0185863 A1* | 10/2003 | Bengs .................. B01J 13/0065 424/401 |
| 2003/0215585 A1 | 11/2003 | Bunick |
| 2004/0087669 A1 | 5/2004 | Hausmanns et al. |
| 2007/0275024 A1 | 11/2007 | Hedlv et al. |

(Continued)

FOREIGN PATENT DOCUMENTS

| | | |
|---|---|---|
| CN | 1324620 A | 12/2001 |
| CN | 1432356 A | 7/2003 |

(Continued)

OTHER PUBLICATIONS

Lai L Setal: "Physichchemical Changes and Rheological Properties of Starch During Exttrusion (a Review)" Biotechnology Progress, American Institute of Chemical Engineers, US LNKD-DOI: 10.1021/BP00009A009, vol. 7, No. 3, Jan. 1, 1991 (Jan. 1, 1991), Relevant to claim No. 1-16.
ISSN: 8756-7938 2. Physicochemical Changes in Stucb during Extrusion, Relevant to claim No. 15,16Ha Pushpadas et al: "Macromolecular Chang :s in : xtrud :d Starch-Films Plastkiz :d with Glyc : rul, Water and st : aric Acid" Starchjsrarke, vol. 61, May 13, 2009 (May 13, 2009), pp. 256-266, XP002591655 DOI: 10.1002/star .200800046 2. Material.and Methods, Relevant to claim No. 1.
D. Peressini et al: "Starclt-Methylcelluose based ediable films; rheological properties of film forming dispersions" Journal of Food Engineering, vol. 59, 2003, pp. 25-32, XP002591656 the wbole document. Revelant to claim No. 1-16.

(Continued)

*Primary Examiner* — Adam C Milligan
(74) *Attorney, Agent, or Firm* — Knobbe, Martens, Olson & Bear, LLP

(57) ABSTRACT

A method for producing starch soft capsules comprises the following steps: preparing a mixture comprising starch, plasticizer and water, wherein more than 50 weight percent of the starch is present in the form of particles of granular starch; shaping the mixture to form a film in a shaping process; solidifying the mixture by increasing the temperature of the mixture during and/or after the shaping process by more than 5° C.; and shaping the film to form a soft capsule. Soft capsules produced by this method have starch particles bonded to one another. A device for performing this method comprises a shaping device to enable shaping of the starch material to form a film, and a heating device to perform a heat treatment to destructure the starch during and/or after the shaping. It comprises a rotary die device.

7 Claims, 6 Drawing Sheets

(56) References Cited

U.S. PATENT DOCUMENTS

| | | |
|---|---|---|
| 2009/0068333 A1 | 3/2009 | Muller et al. |
| 2011/0319503 A1 | 12/2011 | Muller et al. |
| 2012/0006226 A1 | 1/2012 | Muller et al. |

FOREIGN PATENT DOCUMENTS

| | | |
|---|---|---|
| CN | 1486687 A | 4/2004 |
| DE | 19943604 A1 | 3/2001 |
| EP | 0 118 240 | 9/1984 |
| EP | 0546538 A1 | 6/1993 |
| EP | 0546539 A1 | 6/1993 |
| JP | 2003-55198 A | 3/2003 |
| JP | 2005-112849 | 4/2005 |
| JP | 2005-170929 | 6/2005 |
| WO | WO 01/03677 A1 | 1/2001 |
| WO | WO 2004/085483 A2 | 10/2004 |
| WO | WO 2007/128150 A1 | 1/2007 |
| WO | WO 2008/105662 A1 | 9/2008 |
| WO | WO 2010/100196 | 9/2010 |

OTHER PUBLICATIONS

IB, International Search Report, PCT!EP2010/52702, dated Jul. 13, 2010.

Roy L Whistler et al. (Editors): "Starch: Chemistry and Technology", 1984, Academic Press, Inc., Orlando, Seiten 292 and 666.

International Preliminary Report on Patentability PCT/NL2008/050120 dated Sep. 1, 2009.

Lai et al., Physicochemical Changes and Rheological Properties of Starch during Extrusion ( a Review), Biotechnol. Prog. 1991, 7, 251-266, relevant to claims 15 and 16.

Restriction Requirement issued in U.S. Appl. No. 13/255,045, dated Dec. 17, 2014, in 10 pages.

Office Action issued in U.S. Appl. No. 13/255,045, dated Feb. 26, 2015, in 10 pages.

Final Office Action issued in U.S. Appl. No. 13/255,045, dated Aug. 31, 2015, in 15 pages.

Pushpadass et al., "Effects of Extrusion Temperature and Plasticizers on the Physical and Functional Properties of Starch Films," *Starch/Stärke*, vol. 60, pp. 527-538 (2008).

Thomas et al., "Gelatinization, Pasting, and Retrogradation," Starches, Eagan Press Handbook Series, Ch. 3, (1997).

IB, International Search Report, PCT/EP2010/052717, dated Jul. 13, 2010.

IB, International Search Report, PCT/NL2008/050120, dated May 13, 2008.

Thomas et al., "Starches," Eagen Press Handbook Series (1997).

\* cited by examiner

SOFT CAPSULE BASED ON STARCH AND A METHOD AND DEVICE FOR THE PRODUCTION THEREOF

CROSS REFERENCE TO RELATED APPLICATION

The application is a continuation application of U.S. patent application Ser. No. 13/255,072, filed Sep. 9, 2011.

The present invention relates to a method, in particular a casting method, for producing soft starch capsules, the resulting soft capsules and a device for producing inventive soft capsules.

STATE OF THE ART

Soft capsules are used to hold, for example, pharmaceutical active ingredients, dietary products and food supplements. The shell of a soft capsule usually consists mainly of gelatin, which is why the capsules are often also referred to as soft gelatin capsules. Although gelatin is used almost exclusively, this substance has numerous disadvantages. Gelatin is a material of animal origin and thus became the subject of objections and public criticism for the first time in conjunction with the BSE crisis. Since then there has been an intense search for plant-based alternatives. Since the BSE crisis, there have been repeated new objections in an environment of recurring meat scandals, and in general there has been a growing trend toward vegetarian approaches. Gelatin capsules are therefore undesirable for vegetarians and are unacceptable for vegans. Since gelatin is obtained mostly from slaughterhouse waste from pigs, gelatin capsules are also unacceptable for consumers who need kosher or halal products.

The desired gelatin substitute in the area of soft capsules should preferably be of plant origin, should enable the production of capsules with the same quality as that known for gelatin, the alternative raw material should not be more expensive, the process should not be more complex and/or expensive and the new technology should not require a major investment.

U.S. Pat. No. 6,770,293 proposes shells of soft capsules based on copolymers of polyvinyl esters and polyesters. However, these are synthetic polymers. However, in the field of soft capsules, there is the desire to replace gelatin, which has the previously been predominant, by alternative substances on a plant basis.

U.S. Pat. No. 5,342,626 describes the production of gelatin-free soft capsules, which are based on a mixture with the essential ingredients gellan, carrageenan and mannan. The mixture described behaves like gelatin, so it is liquid at high temperatures and forms a film when cooled. U.S. Pat. No. 6,949,256 also describes the production of gelatin-free soft capsules based on carrageenan. It is true that soft capsules produced in this way are based on plant starting materials, but they have the disadvantage that carrageenan is expensive and is also suspected of being carcinogenic. Furthermore, corresponding soft capsules can be produced only with a difficult and sensitive method because of the high viscosity of the melt and the slow rate of gelation of carrageenan, and their properties are definitely inferior to those of soft gelatin capsules.

Another material for producing soft capsules originating from plant sources is starch. Starch is a much less expensive raw material than gelatin. However, casting methods for producing soft starch capsules from aqueous starch solutions are limited due to the necessity of using a low starch content and a high water content for such solutions. Mixtures of destructured or dissolved starch typically become so viscous at a starch content of 5% that simple casting methods at least are no longer possible. The reason for this is the extremely high molecular weight of starch, which may be as high as 100,000,000 g/mol.

Mixtures with starch in higher concentrations can also be cast by optionally hydrolyzing the starch that is used so that the molecular weight is reduced and the starch grains are dissolved by boiling and/or shearing. However, then gelation is not obtained in casting and instead the solution gradually solidifies by cooling and slow drying so the production rate remains very low. Furthermore, inferior mechanical properties of the soft capsules are also obtained because the long starch macromolecules have a positive influence on the mechanical properties. For example, U.S. Pat. No. 6,375,981 describes soft cast starch capsules. The hydrolyzed starch that is used is boiled under conditions that lead to a complete destruction of the starch grains.

However, soft starch capsules are usually obtained by extrusion, which requires expensive extruders. A homogeneous starch melt of a high viscosity is produced from the starch which is typically present in a granular form at temperatures of more than 100° C. in plasticization under the influence of mechanical energy in the form of shearing and this starch melt is then pressed through a slotted nozzle under high pressures to first produce a starch film. Due to the high mechanical energy input the molecular weight of the starch is greatly reduced, which is a disadvantage for the mechanical properties of the film, and furthermore, the macromolecules become oriented in the longitudinal direction of the film during the flow processes that take place at the nozzle, so the film is anisotropic, which is a disadvantage for further processing. After shaping there is no gelation when starch films are extruded and instead after the shaping the temperature of the film drops so the strength of the film increases somewhat. This film is then processed further to form soft capsule shells.

Soft capsules produced from homogeneous starch films obtained by extrusion are known from EP 1 103 254 B1, for example. They are complex to manufacture because of the extruders required and the plasticized starch films are difficult to weld, which is why high welding temperatures are needed. The resulting capsules have inferior properties and in particular are fragile at a low atmospheric humidity.

Destructuring of starch is achieved by heating starch in an aqueous medium, wherein the destructuring increases with an increase in temperature. If the starch grains are at the same time subjected to mechanical stress by shearing forces, then a greater destructuring is obtained at the same temperature. If the crystallinity of the starch grains is substantially destroyed, then even minor shearing forces such as those which occur in simple mixing and flow processes of starch mixtures are sufficient to increase the degree of destructuring and to substantially destroy the swollen starch grains, and furthermore, the molecular weight of the starch macromolecules can be significantly reduced. The degree of destructuring can be subdivided into the following stages:
stage 1: the crystallinity of the starch is partially destroyed; in a polarization microscope are
stage 1.1: at most 5% of the grains no longer birefringent
stage 1.2: 5-10% of the grains no longer birefringent
stage 1.3: 10-20% of the grains no longer birefringent
stage 1.4: 20-30% of the grains no longer birefringent
stage 1.5: 30-40% of the grains no longer birefringent
stage 2: the crystallinity of the starch is substantially destroyed; in a polarization microscope are stage 2.1: 40-50% of the grains no longer birefringent
stage 2.2: 50-60% of the grains no longer birefringent
stage 2.3: 60-80% of the grains no longer birefringent
stage 2.4: 80-100% of the grains are no longer birefringent
stage 3: at most 5% of the grains are birefringent
stage 3.1: and 1-10% of the grains have ruptured
stage 3.2: and 10-20% of the grains have ruptured
stage 3.3: and 20-30% of the grains have ruptured
stage 3.4: and 30-50% of the grains have ruptured
stage 3.5: and 50-70% of the grains have ruptured
stage 3.6: and 70-100% of the grains have ruptured
Ruptured starch grains are characterized in that the starch grains have tears/cracks at the surface and/or the previously relatively smooth surface has definitely been deformed (e.g., shrunken surface). In addition to starch particles which are still present in the form of whole grains also starch particles that have disintegrated into fragments may be present. However, the starch grains as well as the fragments are still discernible as entities.
stage 4: no birefringence is observed and the starch grains are substantially destroyed
stage 4.1: there are still fragments of starch grains but the starch is mostly in dissolved form
stage 4.2: the starch is completely in dissolved form There is no uniform understanding of the term "destructured starch" in the technical world. A destructured starch here refers to a starch which has been destructured to stage 4.1 at most, i.e., the starch is still at least partially in the form of particles.

All starch soft capsules produced from solutions of degraded starch or extruded starch materials have in common that the molecular weight of the starch is greatly reduced and the starch particles have been essentially completely destroyed. Consequently, soft capsules produced according to the above-mentioned publications U.S. Pat. No. 6,375,981 and EP 1,103,254 B1 essentially contain only starch of destructuring stage 4.2.

The object of the present invention is to provide a soft capsule based on unobjectionable and favorable plant raw materials having good mechanical properties and being simple and cost-effective in production.

It should preferably be possible to produce the inventive soft capsule using the standard "rotary die" encapsulation method.

The term soft capsule refers to the soft capsule as a whole, i.e., the soft capsule shell plus contents, as well as the soft capsule shell alone and is understood in the text to refer to the soft capsule as a whole and/or the soft capsule shell accordingly.

DESCRIPTION OF THE INVENTION

This object is achieved according to the invention by a method for producing a soft capsule based on starch, in particular by a casting method, in which a mixture comprising starch, in which more than 50 weight percent (wt %) of the starch in the liquid phase is present as particles of granular starch, is shaped into a film, and the mixture is solidified during and/or after this shaping by an increase in temperature, in particular by more than 5° C., and soft capsules are produced from this film.

This object is preferably achieved by a method for producing a soft capsule based on starch, in particular a casting method, comprising the following steps:
preparing a mixture comprising:
a) >40 weight percent of the dry mixture, after subtracting the plasticizer, starch, wherein more than 50 weight percent of the starch in the liquid phase is present in the form of particles of granular starch,
b) 15-70 weight percent of the dry mixture plasticizer,
c) 15-90 weight percent of the total mixture water,
d) optionally at most 50 weight percent of the dry mixture, after subtracting the plasticizer, thickener, and
e) optionally conventional additives and adjuvants,
shaping the mixture to form a film in a shaping operation,
solidifying the mixture by increasing the temperature of the mixture during and/or after the shaping operation by more than 5° C., and
shaping the film to form a soft capsule comprising particles of destructured starch.

According to the invention, the molecular weight of the starch is not impaired significantly. Therefore, especially good mechanical properties of the fresh film, the fresh soft capsule and the dried soft capsule are possible. In addition, however, also the heterogeneous structure of the material contributes significantly to this, in that the destructured particles of granular starch formed at the solidification temperature already have a certain strength and elasticity per se, which has advantageous effects on the handling of the fresh film and the fresh soft capsules as well as the dried soft capsules.

Advantageous embodiments of the invention are contained in the dependent claims.

For good mechanical properties of the starch film, the molecular weight of the starch and its proportional amount in the starting mixture should be large enough. The initially contradictory combination of pourability, i.e., low viscosity, and high molecular weight of the starch is achieved according to the invention by the fact that the starch in the casting mixture is present in the form of particles. Then the viscosity of the mixture is determined primarily by the viscosity of water and plasticizer and is low accordingly. For example, a starch mixture comprising approximately 35 weight percent water in total and 35 weight percent glycerol, based on the starch content, can be cast well, even without pressure. A mixture of the same composition but in which the starch is present in destructured, dissolved or plasticized form prior to shaping would have a viscosity at least 1000 times higher, i.e., more than 10,000 Pas. To shape such a mixture to form a film, high pressures would be needed such as those which can be produced by extruders, for example. Alternatively, the water content of such a mixture would have to be increased to approximately 95% in order for the mixture to be castable without pressure. However, then it would still be a liquid after casting, even with a subsequent temperature increase, and not a film with usable mechanical properties that could be processed further to a soft capsule.

If the starch mixture is heated, there is greater swelling and destructuring of the starch particles, wherein the particles incorporate water and plasticizer, swell and stick together. An agglomerate or conglomerate of particles is obtained, i.e., a heterogeneous structure consisting of a mixture of starch particles.

Solidification of the castable mixture, previously of a low viscosity, to form a viscoelastic solid material, which can be characterized by a typical solid-state property such as the modulus of elasticity, then occurs almost simultaneously with the increase in temperature and occurs due to the fact that the liquid phase of water and plasticizer disappears, i.e., diffuses into the starch particles, a network structure, i.e. a gel structure within the starch particles is formed due to the entanglement of macromolecules, and the particles are stuck to one another. Optionally, the sticking of the particles can still be modified by adding a thickener.

Solidification of the mixture is understood to refer to the primary solidification, wherein there is a destructuring of granular starch, i.e., a phase conversion of the starch and the properties of the mixture change by orders of magnitude. This phase conversion is manifested as gelation of the casting compound/casting material to form a solid film. This does not require any gelling agents other than starch. After the primary solidification of the mixture, there is a secondary solidification, which is accompanied by a gradual change in the properties of the substance when the temperature of the film, which has solidified primarily, and/or its water content is/are reduced and/or a gradual formation of a network of the starch occurs, induced by retrogradation, i.e., crystallization of the starch macromolecules.

According to the invention, mixtures of starch with high starch proportions can be processed to soft capsules using simple casting methods. In comparison with a mixture in which the same amount of starch is present in dissolved form, lower viscosities of the mixture are obtained by several orders of magnitude. Solidification of the mixture to an isotropic soft capsule material of a high elasticity and high extensibility is achieved through an increase in temperature. It is advantageous that the molecular weight of the starch is not impaired significantly in the inventive method. Preferably the $M_w2/M_w1$ quotient is >0.3, more preferably >0.4, more preferably >0.5, more preferably >0.6, more preferably >0.7, more preferably >0.8, where $M_w1$ is the weight-average molecular weight distribution of the starch used and $M_w2$ is the weight-average molecular weight distribution of the starch in the soft capsule produced. It should be noted here that the molecular weight of starch shows a very sensitive reaction to mechanical stress. For example, the molecular weight of dissolved starch is measurably reduced merely by shaking the solution.

The starch mixtures to be used according to the invention may be processed to soft capsules in almost the same way as is the case with gelatin-casting methods. This is an especially favorable prerequisite for replacing gelatin soft capsules because the same installations and equipment can be used. The difference in comparison with gelatin soft capsules from the standpoint of the process technology consists essentially of the fact that gelatin melts will undergo gelation when cooled, whereas the starch mixture according to the invention undergoes gelation due to an increase in temperature. The soft capsules according to the invention not only have the known quality of soft gelatin capsules, but also the method so far is not more complex and the new technology does not require greater investments. Instead, the complex processing of the gelatin melt is eliminated and/or can be replaced by a simple mixing operation.

Starch

With regard to the origin and processing, generally any starches or mixtures thereof may be used. For example, they may be used in the native state as well as in a physically and/or chemically/enzymatically modified state.

With regard to the origin, root starches, for example, potato starches or tapioca starches are preferred because they have low gelatinization temperatures in comparison with starches of other origin and the solidification and/or gelation of the casting composition to form films for the production of soft capsules is therefore possible even at low temperatures. Tapioca starch is especially preferred. Tapioca starch is colorless, tasteless, has a very good transparency and no genetically modified variants of tapioca starches are known.

In a preferred embodiment, the starch is used in the native, i.e. unmodified state. Good properties can be achieved at a low cost in this way.

In another preferred embodiment, substituted starches such as starch esters and starch ethers are used, for example, hydroxypropylated or acetylated starches. These modifications lead to especially high transparency and high extensibility of the film.

Oxidized starches are used as an alternative.

In another preferred embodiment, crosslinked starches are used, in particular crosslinked starch esters and/or crosslinked starch ethers, for example, starch phosphates and starch adipates. By increasing the molecular weight, which is associated with crosslinking, improved mechanical properties are obtained and the starch grains are also stabilized mechanically as units, which is especially advantageous for the process because the contribution of the starch particles to the mechanical properties of the fresh film, of the fresh soft capsule and of the dried soft capsule can be increased in this way. In the case of highly crosslinked starches, the destructured starch grain practically forms a molecule of a gigantic molecular weight and has a particularly high stability.

In another preferred embodiment, substituted tapioca starch is used, in particular crosslinked substituted tapioca starch, for example, hydroxypropylated starch phosphate.

The preferred weight-average molecular weight distribution $M_w1$ of the starch used is at least 500,000 g/mol, especially preferably at least 1,000,000 g/mol, more preferably at least 2,500,000 g/mol, even more preferably at least 3,000,000 g/mol, even more preferably at least 4,000,000 g/mol, even more preferably at least 5,000,000 g/mol, even more preferably at least 7,000,000 g/mol, most especially preferably at least 10,000,000 g/mol.

The amylose content of the starches in weight percent is preferably <50, more preferably <40, more preferably <35, more preferably <30, more preferably <27, more preferably <25, most especially preferably <20. High amylose contents lead to a reduced extensibility of the film and the resulting soft capsules are of a lower quality with respect to gloss and transparency. Furthermore, its disintegration properties in an aqueous medium are worsened.

In addition, waxy starches, in particular crosslinked and/or substituted waxy starches are preferred. Waxy starches are advantageous with regard to transparency.

The amylose content of the starches in weight percent is preferably >=0, more preferably >0.3, more preferably >0.5, more preferably >0.7, more preferably >1, more preferably >2, most especially preferably >3. If the amylose content is too low, it may lead to reduced extensibility of the film.

Also preferred are starches with a gelatinization temperature <90° C., especially preferably <80° C., more preferably <75° C., more preferably <70° C., more preferably <67° C., most especially preferably <65° C. The gelatinization temperature is determined by DSC (differential thermal calorimetry) as the peak temperature in heating a starch/water mixture comprising 65 weight percent of water at a rate of 10° C./min. With a decline in gelatinization temperature, the solidification of the cast film at lower temperatures becomes possible and thus both easier and faster.

Starches with a dextrose equivalent (DE) of <10, especially preferably <1, most preferably <0.7, more preferably <0.5, more preferably <0.2, more preferably <0.1, most especially preferably <0.05 are also preferred. The dextrose equivalent of a polysaccharide mixture refers to the percentage amount of reducing sugars in the dry substance. It corresponds to the amount of glucose (=dextrose), which would have had the same reducing power per 100 g dry substance. The DE value is a measure of how far the degradation of the polymer has proceeded, so all products with a low DE value have a large amount of polysaccharides and a small amount of low molecular sugars (oligosaccharides) whereas products with a high DE value consist mainly only of low-molecular sugars. The dextrose equivalent is determined according to ISO standard 5377. The strength of the soft capsule increases after solidification as the DE value becomes lower.

In a preferred embodiment of the invention, the starch content of the dry mixture, after subtracting the plasticizer (i.e., after mathematical subtraction of the plasticizer from the dry mixture consisting of starch, plasticizer and all the optional components), in weight percent is >40, especially preferably >50, more preferably >60, more preferably >70, more preferably >80, more preferably >90, especially preferably >95.

Granular Starch

The granular starch is preferably used with a destructuring of up to 2.2, more preferably up to stage 2.1, more preferably up to stage 1.5, more preferably up to stage 1.4, more preferably up to stage 1.3, more preferably up to stage 1.2, more preferably up to stage 1.1, most especially preferably in the native undestructured state. The viscosity of the mixture declines with a decline in destructuring, so that the casting is simplified.

According to the invention, the granular starch is used in the form of particles, which particles correspond in their shape to the original starch grains or are agglomerates thereof. Typical sizes of the starch grains in the unswollen state are 5-100 μm for potato starch, 5-30 μm for corn starch, 1-45 μm for wheat starch, 4-35 μm for tapioca starch, 1-30 μm for rice starch. In a partial destructuring, the original starch grains may have been altered with regard to geometry and size, in particular with a definite increase in size in destructuring. As granular starch also mixtures of various granular starches may be used.

The amount of granular starch in weight percent in the total starch content of the mixture is preferably >60, especially preferably >70, more preferably >75, more preferably >80, more preferably >85, most especially preferably >90.

Water

Water is important in adjusting the viscosity of the casting compound and in solidification of the soft capsules after shaping the casting composition to form a film. The greater the water content, the simpler is the casting, the more rapidly is the solidification and the less is the temperature increase required to accomplish this. On the other hand, a high water content reduces the strength of the soft capsules and longer drying times are needed because then more water must be removed from the film and/or the soft capsule.

The upper limit for the water content of the casting composition in weight percent is preferably 90, especially preferably 80, more preferably 70, more preferably 60, more preferably 50, more preferably 45, most especially preferably 40, while the lower limit of the water content of the casting composition in weight percent is preferably 15, especially preferably 20, more preferably 25, more preferably 30, most especially preferably 33. With an increase in the water content, solidification is facilitated, e.g., made possible and/or accelerated at lower temperatures, but the strength of the solidified film is reduced and the amount of water that must be removed again after solidification is increased.

Plasticizer

Generally all the plasticizers for starch known in the state of the art may be used as plasticizer. A low plasticizer content leads to embrittlement of the soft capsules at low atmospheric humidity levels, whereas a high plasticizer content leads to inferior properties at a high atmospheric humidity.

Plasticizers may be used individually or in mixtures of various plasticizers. Polyols such as glycerol, sorbitol, maltitol, erythritol, xylitol, mannitol, galactitol, tagatose, lactitol, maltulose, isomalt, maltol, etc. are preferably used, but also various sugars such as sucrose, maltose, trehalose, lactose, lactulose, galactose, fructose, etc. as well as mono- and oligosaccharides. Glycerol is especially preferred as a plasticizer. In addition to its property as a plasticizer, sucrose also has the advantage that it improves the oxygen barrier properties of the soft capsule. Water is also a plasticizer for starch but is not counted with the plasticizers here and is taken into account separately.

The upper limit for the plasticizer content in weight percent of the dry mixture preferably is 70, especially preferably 60, more preferably 55, more preferably 50, more preferably 46, most especially preferably 42, whereas the lower limit in weight percent is preferably 15, more preferably 20, more preferably 25, more preferably 28, more preferably 31, more preferably 32.5, most especially preferably 33.5.

In a preferred embodiment, plasticizers with a maximum melting point of the anhydrous plasticizer of 150° C., preferably 125° C., especially preferably 110° C., more preferably 95° C., most especially preferably 70° C. are used. The amount of plasticizer in the total plasticizer content which meets this condition is in weight percent>50, preferably >70, especially preferably >80, most especially preferably >90.

Optional Components of the Starch Mixture

Short-Chain Amylose

The starch mixture may comprise an amount of short-chain amylose. This short-chain amylose may be obtained in the granular starch, for example, by the action of enzymes on the granular starch or may be applied to the granular starch by spraying the granular starch with dissolved short-chain amylose. This short-chain amylose may be supplied together with at least one of the starches which is used to produce the film or it may be added separately to the mixture, for example, in the form of a solution of short-chain starch or in the form of spray-dried short-chain starch, where the spray-dried short-chain starch may have other spray-dried starches than those in the mixture. The short-chain amylose is preferably present in and/or on the granular starch in non-crystalline form.

Short-chain amylose consists of substantially unbranched amyloses and is used in a preferred embodiment. The degree of branching (number of branches per monomer unit) of the short-chain amyloses is <0.01, preferably <0.005, especially preferably <0.003, more preferably <0.001, more preferably <0.0007, more preferably <0.0004, most especially preferably <0.0001. Ideally the short-chain amylose has a degree of branching of 0 or close to zero, for example, when it is obtained by complete debranching (for example, by means of pullulanase). With the decline in the degree of branching, the crystallizability of the short-chain amylose and thus also the formation of a network (by heterocrystallization with longer starch macromolecules) increases, which is effected by the short-chain amylose. With an increase in formation of network, improved properties of the inventive soft capsules are obtained, in particular higher modulus of elasticity values at high atmospheric humidities, so that the soft capsules can be used in a wide range of climate zones with different atmospheric humidities.

Short-chain amylose has an average degree of polymerization (DPn: number-average) of >8 and <500. According to the invention it is preferably <300, especially preferably <100, more preferably <70, more preferably <50, most especially preferably <30. In addition it is preferred according to the invention that the average degree of polymerization is >10, especially preferably >12, more preferably >14, most especially preferably >15. With a decline in DPn the transparency of the soft capsules is improved because the heterocrystallites consisting of short-chain amylose and longer starch macromolecules become smaller with a decrease in the DPn of the short-chain amylose so that the light scattering is reduced. If the DPn is too low crystallization is no longer possible.

Short-chain amylose can be obtained, for example, by polymerization of glucose synthetically or from starch by the action of enzymes (for example, α-amylase, β-amylase, isoamylase, pullulanase).

The amount of short-chain amylose in the total starch content of the mixture in weight percent is preferably <15, especially preferably <10, more preferably <7.5, more preferably <5, more preferably <3, most especially preferably =0.

Thickeners

A thickener may be added to the mixture comprising starch to adjust the viscosity of the mixture at a desired level, so it permits optimization of the viscosity of the mixture in casting. Furthermore, thickeners are advantageously used to weaken the bonds between the destructured starch particles in the solidified soft capsules with regard to an accelerated decomposition behavior in an aqueous medium. The thickener may be present in the form of particles, in swollen form or in dissolved form at the time of shaping of the mixture.

Generally all hydrophilic substances and mixtures thereof may be used as thickeners if they increase the viscosity, in particular hydrophilic polymers and, of those, preferably those of plant sources. Examples include hydrocolloids and gums such as galactomannans, e.g., guar gum or locust beam gum; cellulose derivates; pectins, in particular rhamnogalacturonans and protopectins; dextrans; xanthan; zymosan; hydrocolloids from marine algae, such as alginates, agar, agarose, carrageen and carrageenans; furcellaran; hydrocolloids from lichens, such lichenins and isolichenins or hydrocolloids as exudates from woods, such as gum tragacanth (*astragalus* gum), karaya gum, gum arabic, kutira gum; inulin; latex; chitin; chitosan; gellan; collagen; gelatin; casein. Dissolved starch may be used for the same functionality as the thickeners but it is not counted with the thickeners and is treated separately.

Some of these thickeners, for example, gelatin, carrageenan, gellan and pectin are also known as gelling agents, but they gel when cooled instead of when heated. They do not make any contribution toward gelation in the solidification of the inventive casting mixture with an increase in temperature, nor are they used for this purpose.

In a preferred embodiment, the maximum amount of thickener in weight percent, based on the dry recipe, after subtracting the plasticizer is 50, more preferably 40, more preferably 30, more preferably 20, more preferably 10, more preferably 5, more preferably 2.5, most especially preferably 1.

In another preferred embodiment, the maximum amount of carrageen and carrageenans in weight percent, based on the dry recipe, after subtracting the plasticizer is 10, more preferably 7.5, more preferably 5, more preferably 3, more preferably 2, more preferably 1, more preferably 0.5, most especially preferably 0. Because of the high cost of raw materials and the suspected carcinogenicity, the amount of carrageen and carrageenans is kept as low as possible.

In another preferred embodiment, the maximum amount of gelatin in weight percent, based on the dry recipe, after subtracting the plasticizer is 10, more preferably 7.5, more preferably 5, more preferably 3, more preferably 2, more preferably 1, more preferably 0.5, most especially preferably 0. Because of the general gelatin problems, the amount of gelatin is kept as low as possible.

In another preferred embodiment, the maximum amount of gellan in weight percent, based on the dry recipe, after subtracting the plasticizer is 5, more preferably 2.5, more preferably 2, more preferably 1.5, more preferably 1, more preferably 0.5, more preferably 0.2, most especially preferably 0. The amount of gellan is kept as low as possible because of the high cost of raw materials.

In another preferred embodiment, the maximum amount of pectin in weight percent, based on the dry recipe, after subtracting the plasticizer is 5, more preferably 2.5, more preferably 2, more preferably 1.5, more preferably 1, more preferably 0.5, more preferably 0.2, most especially preferably 0. The amount of pectin is kept as low as possible because of the high cost of raw materials and the problems in processing.

In another preferred embodiment, the maximum amount of cellulose derivatives in weight percent, based on the dry recipe, after subtracting the plasticizer is 15, more preferably 10, more preferably 5, more preferably 2.5, more preferably 1, more preferably 0.5, most especially preferably 0. The amount of cellulose derivatives is kept as low as possible because of the high cost of raw materials and the separation and/or precipitation of cellulose derivatives from the starch mixture at increased temperatures.

Dissolved Starch

Dissolved starch may be used like the thickeners mentioned above to increase the viscosity of the mixture and to modify the bond between the starch particles. Its use is optional because the desired increase in viscosity to a viscosity suitable for casting can also be achieved through a suitable increase in the temperature of the casting mixture, where the granular starch increases the viscosity due to swelling. However, the temperature of the casting mixture must be adjusted and controlled accurately so the procedure when using dissolved starch (or a thickener) is simpler and is therefore preferred.

With regard to dissolved starch, the same statements apply as with regard to suitable starches and preferred types such as those pertaining to starch in general. However, dissolved starch may also have a lower molecular weight than is generally preferred for the starch. Furthermore, highly retrogradation-stabilized starches, for example highly substituted starches or highly branched dextrins, are also preferred for the dissolved starch so that the disintegration of the soft capsule in an aqueous medium can be accelerated.

Dissolved starch differs from granular starch in its condition in the casting mixture where it is present in dissolved form or in a predominantly destructured form while the granular starch at this point in time is still primarily not destructured.

Dissolved starch may be obtained, for example, by dissolving amorphous extruded starch or it may be obtained from pregelatinized starch. According to the invention the term "dissolved starch" is also understood to include pregelatinized starch (such as, for example, roll-dried pregelatinized starch) even if this is present in undissolved form or is only partially dissolved. Pregelatinized starch is preferably destructured at least to stage 2.3, more preferably at least to stage 2.4, even more preferably at least to stage 3.1, even more preferably at least to stage 3.3.

In a preferred embodiment, dissolved starch is destructured at least to stage 2.3 at the latest by the time when the mixture is shaped into a film, even more preferably at least to stage 2.4, more preferably at least to stage 3.1, more preferably at least to stage 3.3, more preferably at least to stage 3.5, more preferably at least to stage 3.6, especially preferably at least to stage 4.1, most especially preferably up to stage 4.2.

In addition, it is preferable according to the invention for the upper limit for the amount of dissolved starch in weight percent, based on the anhydrous mixture, to be 30, especially preferably 25, more preferably 20, more preferably 15, more preferably 10, most especially preferably 5.

Additional Components (Additives and Adjuvants)

Additional components of the starch mixture may include dyes and pigments as well as fillers, mineral fillers, for example, talc, or modifying substances such as polyethylene glycols or disintegration aids, for example, carbonates or bicarbonates or additives, for example, preservatives, antioxidants or emulsifiers, for example, lecithins, mono-, di- and triglycerides of fatty acids, polyglycerol esters, polyethylene esters or sugar esters. Generally all additives which are used in soft gelatin capsule shells may also be used according to the invention, in particular additives which are used to adjust the soft capsule shell to the ingredient (formulation adjuvants).

Shaping and Solidification

The starch in the form of particles of granular starch is destructured during and/or after the shaping of the mixture to form a film by an increase in temperature so that rapid solidification of the casting mixture to form a solid film is obtained.

The temperature increase preferably takes place after the mixture is shaped to form a film, in particular immediately after the shaping of the mixture to form a film. The temperature increase during the shaping optionally amounts to at most 50%, preferably at most 40%, more preferably at most 30%, more preferably at most 20%, most preferably at most 10% of the total temperature increase of the casting compound to the solidification temperature.

In a preferred embodiment, the mixture comprising starch may be shaped under a pressure of less than 5 bar (0.5 MPa), especially preferably less than 4 bar (0.4 MPa), more preferably less than 3 bar (0.3 MPa), more preferably less than 2 bar (0.2 MPa), most especially preferably less than 1 bar (0.1 MPa). At such pressures, the pressure buildup is simple and the equipment required is also simple and favorable. In yet another preferred embodiment, the mixture comprising starch may be shaped at a pressure of less than 0.7 bar (0.07 MPa), especially preferably less than 0.6 bar (0.06 MPa), even more preferably less than 0.5 bar (0.05 MPa), more preferably less than 0.4 bar (0.04 MPa), more preferably less than 0.3 bar (0.03 MPa), most especially preferably less than 0.2 bar (0.02 MPa). In the most preferred embodiment, the mixture is shaped under practically no pressure, i.e., the mixture flows due to its inherent weight through the shaping unit which is a spreader box, for example, which is the standard equipment used in casting gelatin.

The viscosity of the casting mixture may generally also be set so high, with thickeners for example, that pressures far above 5 bar (0.5 MPa) are necessary for shaping the casting mixture to form a film.

The upper limit for the dynamic viscosity of the mixture before or during shaping (i.e., the viscosity at the corresponding temperature) in Pas is preferably 3000, especially preferably 1000, more preferably 500, more preferably 300, more preferably 200, more preferably 150, more preferably 120, more preferably 100, more preferably 70, most especially preferably 50. In addition, it is preferable for the lower limit for the dynamic viscosity of the mixture before or during shaping in Pas to be 0.01, especially preferably 0.05, more preferably 0.1, more preferably 0.5, most especially preferably 1. The viscosities are based on the shear rate of 1.1/s. High viscosities correlate with the need for high pressures so that the advantages of the low viscosities correspond to the advantages of the lower pressures. Since there are a number of possibilities of shaping mixtures with a wide range of viscosities, the viscosities in question cover a wide range accordingly. In the case of a viscosity below approximately 300 Pas, pressureless casting methods (under the inherent weight of the mixture) by means of the spreader box typically used for the gelatin casting method are possible. The lower limits are defined by the fact that the shaping and in particular the adjustment of the thickness of a cast film become increasingly difficult at very low viscosities (the mixture flows away).

The upper limit for the temperature in ° C. at which the mixture comprising starch is shaped is preferably 90, especially preferably 80, more preferably 70, more preferably 65, more preferably 60, more preferably 55, most especially preferably 50. In addition, in a preferred embodiment, the lower limit for the temperature in ° C. at which the mixture comprising starch is shaped is −20, especially preferably −10, more preferably 0, more preferably 10, more preferably 20, more preferably 30, more preferably 35, more preferably 40, most especially preferably 45.

Starting from the temperature of the casting compound before shaping, i.e., the temperature of the casting compound in the spreader box, the temperature of the starch mixture is increased to solidify it. The lower limit for the temperature increase of the starch mixture in ° C. to induce solidification is preferably 10, especially preferably 15, more preferably 20, more preferably 25, more preferably 30, more preferably 35, most especially preferably 40. In addition, in a preferred embodiment, the upper limit of the temperature increase in ° C. is 130, more preferably 110, more preferably 90, most especially preferably 70. With an increasing temperature increase the solidification is accelerated and better mechanical properties are obtained because the starch particles are better bonded to one another. The upper limit is determined by the bubbling, which occurs and/or increases with an increase in temperature.

The water content after shaping the casting compound during the solidification of the product is preferably kept approximately constant, in particular until the film (at room temperature) has reached a modulus of elasticity in MPa of at least 0.001, preferably 0.003, especially preferably 0.005, more preferably 0.007, more preferably 0.009, most especially preferably 0.01. During the solidification the water content is preferably reduced by at most 25 weight percent, especially preferably by at most 20 weight percent, more preferably by at most 15 weight percent, more preferably by at most 10 weight percent, more preferably by at most 7 weight percent, more preferably by at most 5 weight percent, most especially preferably by at most 3 weight percent (for illustration: the water content after shaping the casting compound to form a film is 40%, so the water content after a 3% reduction is 37%). The constancy of the water content during solidification of the film facilitates the solidification but if the water content is reduced too greatly during this phase it leads to incomplete solidification of the film and thus to inadequate mechanical properties and in particular the film then tends to develop tears and cracks in further processing.

Soft Capsules

Inventive soft capsules based on starch preferably include:

a) >40 weight percent of the dry soft capsule, after subtracting the plasticizer, starch,
b) 15-70 weight percent of the dry soft capsule plasticizer, and
c) 0.1-50 weight percent of the total soft capsule water,
d) optionally at most 50 weight percent of the dry soft capsule, after subtracting the plasticizer, thickener, and
e) optionally conventional additives and adjuvants, where the soft capsules comprise starch particles bonded to one another, in particular particles of destructured starch bonded to one another. The starch particles bonded to one another preferably form a matrix, and additional phases are optionally included in this matrix. The amount of additional phases in weight percent is preferably <30, more preferably <20, more preferably <10, more preferably <5, more preferably <2.5, most preferably <1.5.

These starch particles in the soft capsules are destructured starch particles formed from granular starch in gelation of the casting mixture to form the film, and destructured starch particles that were already in this state before gelation of the casting mixture and originated from the dissolved starch (where their degree of destructuring preferably corresponds at least to that of the granular starch) may optionally also be present.

The starch particles of the granular starch preferably still exist as individual starch particles, especially with an average diameter of at least 2 μm, more preferably at least 4 μm, more preferably at least 6 μm. The starch particles formed from granular starch are preferably destructured at least to stage 2.1, especially preferably up to stage 2.2, more preferably up to stage 2.3, more preferably up to stage 2.4, most especially preferably up to stage 3.1. With an increase in destructuring, the handling of the fresh film and the mechanical and optical properties of the fresh and dried soft capsule are improved. On the other hand, the starch particles are preferably destructured at most up to stage 4.1, especially preferably up to stage 3.6, more preferably up to stage 3.5, more preferably up to stage 3.4, more preferably up to stage 3.3, most especially preferably up to stage 3.2. To achieve a very high destructuring, very high temperatures are necessary in solidification, which is complicated to monitor and control in terms of the process engineering, in particular control of the water content as well as the formation of unwanted air bubbles. Furthermore, at a very high degree of destructuring, when the starch grains are increasingly disintegrating, the positive contribution of the starch particles to the mechanical properties of the fresh film and of the soft capsules decline.

The granular starch is present as solid, at most partially swollen particles at the time of shaping of the mixture to yield a film. This starch is present in the solidified film in the form of severely swollen destructured starch particles which are bonded together either directly by coupling of surfaces of such particles or indirectly via an intermediate layer, where this intermediate layer may optionally comprise a binder and/or starch, in particular dissolved starch. The ratio of the average thickness of the intermediate layer divided by the average diameter of the swollen particles is preferably <0.4, especially preferably <0.2, more preferably 0.15, more preferably <0.1, more preferably <0.05. In other words the particles are preferably densely packed, most preferably the particles come in contact with one another in a dense packing, in particular in an extremely dense packing (i.e., a packing without intermediate spaces).

The bond between the starch particles may optionally be improved by the dissolved starch between the particles or by another binder, but an adequate bond is achieved even without this measure. The structure of the starch film and/or of the soft capsule as a dense agglomerate of particles is clearly manifested when the film and/or the soft capsule is/are placed in water and moved with a magnetic stirrer, for example, at room temperature or at 70° C. The soft capsule disintegrates, optionally under the influence of a slight rubbing (at room temperature), initially to form a fine uniform paste. If this material is further diluted with water, individual starch particles may again be obtained from it and can be identified by their shape under a light microscope as swollen particles of destructured starch. The origin and/or type of starch used can even be determined from destructured starch grains, which can be recovered from the soft capsule, because different starches have different grain shapes and grain size distributions. To make the particles visible under the microscope, they are advantageously stained with an iodine solution (Lugol's solution). Another possibility of revisualizing the original starch particles is placing one drop of the material diluted with water on a microscope slide instead of staining. After the water has evaporated, the starch particles can be identified under the light microscope. Because of the shrinkage of the swollen starch particles in drying, these particles have characteristic deformations and optionally tears.

The preferred weight-average molecular weight distribution $M_w2$ of the comprised starch, like the preferred weight-average molecular weight distribution $M_w1$ of the starch in the starch casting mixture, is at least 500,000 g/mol, especially preferably at least 1,000,000 g/mol, more preferably at least 2,500,000 g/mol, even more preferably at least 3,000,000 g/mol, more preferably at least 4,000,000 g/mol, more preferably at least 5,000,000 g/mol, more preferably at least 7,000,000 g/mol, most especially preferably at least 10,000,000 g/mol.

With regard to the ingredients of the soft capsule, except for the water content, statements regarding the casting mixture used in the method are applicable. The upper limit for the water content of the soft capsule according to the invention in weight percent is preferably 40, especially preferably 30, more preferably 25, more preferably 20, most especially preferably 17, while the lower limit of the water content of the soft capsule in weight percent is preferably 1, especially preferably 3, more preferably 5, most especially preferably 7. As the water content increases, the soft capsule loses its mechanical properties, and in particular becomes too soft. The soft capsule becomes too hard as the water content is lower.

Insoluble Components of the Film and/or the Soft Capsule

The films and/or soft capsule shells produced consist of particles of starch which are packed densely in a preferred embodiment, which yields advantageous properties for the processing of the film and for the properties of the finished film. These particles of starch can be separated, for example, from the soluble components (which include in particular plasticizer, soluble starch, optionally thickeners) by dissolving the film at 70° C. for 30 minutes, and their quantitative amount in the film can thus be measured.

Recovery Method No. 1

In a preferred embodiment, the minimal amount in weight percent of the starch in the soft capsule shell, which can be recovered after dissolving the soft capsule at 70° C. for 30 minutes is 30, preferably 40, more preferably 50, more preferably 55, more preferably 60, more preferably 65, most especially preferably 70%.

Recovery Method No. 2

In another preferred embodiment, the amount of the material which can be recovered after dissolving the soft capsule shell at 70° C. for 30 minutes is determined and is based on the mass of the dry film. The determination according to this definition is simpler than that according to recovery method no. 1 because it can also be used when the composition of the soft capsule shell is not known exactly. The minimal amount in weight percent of the material which can be recovered is 25, preferably 35, more preferably 40, more preferably 45, most especially preferably 50.

Advantages of the Inventive Method and the Inventive Soft Capsules

Casting mixtures according to the invention are simple to produce (invention: simple mixing operation; gelatin: complex gel preparation; thermoplastic starch (TPS): preparing granules, which are difficult to handle because of stickiness and lumping). However, the casting process per se is advantageously like that for gelatin, i.e., pressureless casting under inherent weight is possible, so that switching from gelatin casting to the inventive method is possible, but the solidification takes place through an increase in temperature and not due to a reduction in temperature. Due to the rapid solidification (gelation) after casting, high and competitive production rates are obtained. The film is isotropic like a gelatin film, i.e., its properties do not depend on direction.

The essential feature of the starch mixture, which is used in the inventive method, is that this mixture comprises starch in the form of particles, i.e., the mixture is a dispersion of the particles in an aqueous medium. This mixture is stable over a long period of time.

The encapsulation requires an extensibility of the film of at least 100%. In closing the soft capsule shell, the film should be weldable to itself and the weld should be able to bear load immediately. The fresh capsule should be stable enough for the next processing steps (transport path away from the "rotary die" and cleaning in the tumbler (removal of the rotary die oil). These requirements are fulfilled by the inventive method.

The cost of raw materials and the process costs for the inventive capsule production are lower than those in the production of soft gelatin capsules.

After solidification, the film for producing soft capsules may have a modulus of elasticity of at least 0.009 MPa and an elongation at break of at least 100%. The modulus of elasticity and the elongation at break are measured at room temperature, immediately after solidification, i.e., at most a few minutes after shaping the mixture to form a film, where the water content corresponds to the water content after solidification of the film. If solidification is achieved on a rotary drum, for example, then the modulus of elasticity and the elongation at break of the film are measured after the film has left the drum and the water content in the measurement corresponds to the water content of the film at this point in time. Handling of the film becomes possible only when the modulus of elasticity is high enough and the elongation at break is adequate after solidification because the solidified film is subjected to mechanical stress in the further processing. The properties of the fresh film are more than adequate for this, so high production rates are also possible.

Soft capsules according to the invention also have good mechanical properties, in particular a high elasticity and high extensibility. The soft capsules are composed of densely packed individual starch particles which are bonded to one another/interconnected. These starch particles are present in a swollen state and preferably in a dense packing. The soft capsules are also compact and free of air bubbles. In the past, it has been assumed by the technical world that the starch must be plasticized in the extruder for usable soft capsules, but then the individuality of the starch particles used, typically granular starch, is completely lost.

It is even more surprising in view of the particulate structure, where one would first expect the bonds between the starch particles to be weak points, that an inventive soft capsule actually has better mechanical properties, for example, a higher modulus of elasticity than a soft capsule of the same composition produced by plasticizing the starch in an extruder. The reason for this lies at least partially in the fact that the molecular weight of the starch macromolecules is reduced during plasticization of starch due to the high temperature and/or the high shearing, and the mechanical properties increase with the molecular weight. Since no shearing is needed to produce the inventive film and the temperatures required are definitely lower than those in plasticization, the molecular weight of the starch in the soft capsule corresponds approximately to the molecular weight of the starch before processing (molecular weight determinations usually include a substantial error because the measurements are difficult).

Known soft capsules of transparent plasticized starch become soft and white (opaque) when stored in water but more or less retain their dimensional stability and disintegrate into fragments under a low mechanical stress. There is no dissolving into the original starch particles because their identity has been destroyed in plasticization by means of extrusion.

The difference described here between extruded starch and the starch soft capsules according to the invention also has the advantage that inventive soft capsules disintegrate well in water, dissolve (into the original particles) when seen macroscopically, whereas the extruded soft capsules become soft, but they retain their shape without mechanical action. Thus with the inventive capsules, the contents of the capsule are released more readily and there is a compatibility with pharmacopoeia specifications, which require dissolution of the capsule shell.

Since the particles of the soft capsule shell are densely packed, it has a high density. It is preferably in the range of 1.07-1.3 g/cm$^3$.

When using casting compounds which do not comprise any additives, such as pigments, which reduce transparency, the casting compound, which comprises starch particles and therefore is almost completely opaque, becomes increasingly transparent to the degree as solidification progresses. After solidification is concluded, the soft capsule is then almost completely transparent. This means that writing that can still be read by a person at a distance will still be legible by this person at the same distance when the writing is covered by a transparent film (approximately 0.5 mm thick) for producing the soft capsule, and the font size has been increased by 50% at most.

Inventive soft capsules are stable over a wide range of atmospheric humidities and temperatures, while gelatin soft capsules become very soft at high atmospheric humidities and melt at high temperatures. They have a lower oxygen permeability than gelatin soft capsules.

The good mechanical properties of the inventive soft capsules are a result of the structure of the soft capsule film as an agglomerate of densely packed, destructured starch grains as well as being a result of the high molecular weight of the starch, which is made possible through the inventive method. The destructured starch grains have a certain strength and therefore make a contribution to the good mechanical properties of the soft capsule in a wide range of atmospheric humidities.

Encapsulating Device

The method described here is well suitable for producing soft capsules, because the method is very similar to casting gelatin. When switching from gelatin to starch, this may be done by making changes with reasonable means and the renovations concern mainly only that part of the encapsulating device that pertains to the production of the film. For the additional method steps, certain process parameters must be adjusted, but there are no fundamental changes. It is also advantageous that the operating step of producing the gelatin melt is eliminated and/or can be replaced by the much simpler and faster operating step of producing the starch mixture. This casting mixture is obtained very easily by mixing the components while stirring, wherein the usual simple stirring mechanisms are adequate. For the casting operation, the same spreader box as that used in casting gelatin may be used.

An inventive device for producing soft capsules based on starch therefore comprises the following devices: a shaping device to allow the shaping of a starch material to form a film, at least one heating device to perform a heat treatment for gelation of the starch during and/or after the shaping, as well as a rotary die device, with which the capsules are shaped, filled and unmolded, after the heating device. The inventive device for producing soft capsules optionally still comprises a device for regulating the water content of the film during and/or after shaping, in particular during the solidification of the starch in the area of the heating device.

The characteristic difference between the production of gelatin soft capsules and starch soft capsules is that the molten gelatin casting compound solidifies and/or gels by cooling after casting, whereas on the other hand, the starch casting compound solidifies by an increase in temperature after casting. In the gelatin method, the material is cast on a cooled cylindrical drum at approximately 80° C. (typical temperature approximately 18° C.), whereas in the inventive method, it is preferably cast on a rotating process part, where the increase in temperature of the casting compound is accomplished in particular by thermal conduction. Generally, however, alternatively or additionally, any other type of heating may be used, but in particular heating methods using radiation are suitable, for example, infrared radiation or microwave radiation. Other heating methods use water vapor. The rotating process part is preferably a drum.

The film preferably remains in contact with the rotating process part until the film has essentially solidified completely (primary solidification).

In a preferred embodiment, the film remains in contact with the rotating process part for at least 30% of the circumference of the rotating process part, especially preferably for at least 40%, more preferably for at least 50%, more preferably for at least 60%, most especially preferably for at least 70%.

In a preferred embodiment, the device for regulating the water content of the film regulates the water content so that the water content of the film is reduced during contact with the rotating process part by at most 25 weight percent, especially preferably by at most 20 weight percent, more preferably by at most 15 weight percent, more preferably by at most 10 weight percent, more preferably by at most 7 weight percent, more preferably by at most 5 weight percent, most especially preferably by at most 3 weight percent (for illustration, the water content after shaping the casting compound to form a film is 40% so that after reduction of 3% it is 37%).

In a preferred embodiment, the rotating process part can be heated to a temperature of at least 25° C., especially preferably at least 50° C., more preferably at least 80° C., more preferably at least 90° C., more preferably at least 100° C., most preferably at least 105° C.

The rotating process part preferably has thermal insulation on at least one side.

The device for regulating the water content of the film after shaping in a preferred embodiment comprises a means covering the film on the rotating process part for at least 30% of the circumference, especially preferably for at least 40%, more preferably for at least 50%, more preferably for at least 60%, most especially preferably for at least 70%. The water content in the film is thus regulated during solidification, in particular being kept essentially constant.

This cover is preferably achieved by a corotational belt, which rests on the film and in particular has the same speed or angular velocity as the rotating process part. This belt may have its own drive, but is preferably driven directly with the rotating process part, so that the transfer of force between the rotating process part and/or the film and the belt is accomplished by means of adhesion. The belt may be heated before it comes to lie on the rotating process part and/or the film, for example, heated by radiation such as infrared radiation. One other or multiple heating devices, for example, infrared lamps, may be used along the circumference of the belt around the rotating process part in the area where the belt lies on.

The solidified film is then optionally cooled and then used further like a gelatin film, for example, being oiled and then used for encapsulation by means of rotary dies.

The device for regulating the water content of the film after shaping in another preferred embodiment comprises a means for restricting the space above the film along at least a portion of the rotating process part so that the volume wherein water evaporates out of the film is limited. This restriction preferably pertains to at least 30% of the circumference of the rotating process part, especially preferably at least 40%, more preferably at least 50%, more preferably at least 60%, most especially preferably at least 70%. The restricted volume preferably amounts to at most 10 times the volume of the film within the restriction, especially preferably at most 5 times, more preferably at most twice. In a preferred embodiment, the restricted volume is climatized, i.e., atmospheric humidity and optionally temperature are regulated.

The device for regulating the water content of the film after shaping in another preferred embodiment comprises a means for supplying water to the film, preferably hot water, especially preferably water vapor.

The device for regulating the water content of the film after shaping in another preferred embodiment comprises a means for covering the surface of the film with a liquid. In particular the means produces a film of the liquid on the starch film or the means comprises a bath of liquid through which the starch film is passed. The liquid is preferably an oil.

EXAMPLES

The recipes for the examples are shown in Table 1. Casting mixtures of 10 kg each were prepared. The viscosity of the casting mixture, the mechanical properties and the recovery of the starch are also shown in Table 1.

In all attempts to produce soft capsules, completely transparent soft capsules of a good quality were obtained; in particular, they had dimensional stability, had very good welds, were simple to clean and to dry.

In all the inventive examples, microscopic analysis revealed that the starch films were constructed of densely packed destructured starch grains (<5% birefringent starch grains) and the films could be dissolved into these components again in water, i.e., after disintegration of the films, the destructured starch grains could be detected again in water and their weight could be determined (recovery method no. 1).

Disintegration of the soft capsules in 0.5% hydrochloric acid was determined in an agitated bath at 37° C. on soft capsules that had been dried to a water content of approximately 10% after production and had then been stored for 20 days at 33% atmospheric humidity. The release of the content of the soft capsules occurred after less than 20 min in all examples.

Example 1

According to recipe 1, the water and plasticizer were first added to a heatable and evacuable vessel equipped with a stirrer at room temperature and these two components were then mixed at 100 rpm. Next starch S1E which was extruded under very gentle conditions at a water content of 35% was added and dissolved in the mixture of water and plasticizer for 5 min at 100 rpm. The extruded starch S1E was prepared from dry extrudate (based on the starch S1) by means of a beater mill and had a particle size distribution in the range of 30-150 μmm, as well as a 10% short-chain amylose content (this short-chain amylose was obtained from tapioca starch by complete debranching by means of pullulanase and had a number-average of the degree of polymerization DPn of 25).

To this mixture was then added the granular starch S1 which had a weight-average molecular weight $M_w$ of 30,100,000 g/mol and dispersed therein at 100 rpm for 5 min after which this mixture was heated to 45° C. and degassed for 5 min at 100 rpm by applying a vacuum (removing air bubbles). The dynamic viscosity of this mixture at this temperature was 5.7 Pas at a shear rate of 1.1/s.

Figure 1:
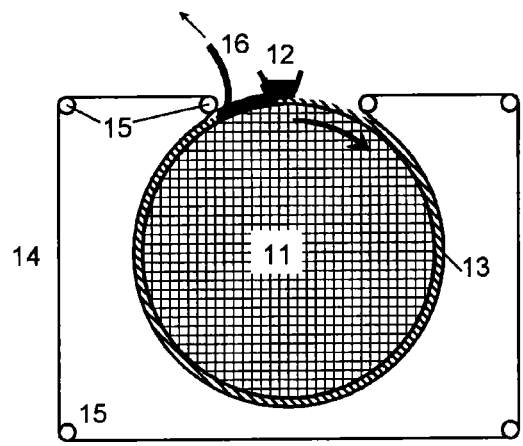
FIG. 1 shows a detail of a first embodiment of the inventive device for producing soft capsules.
Figure 2:
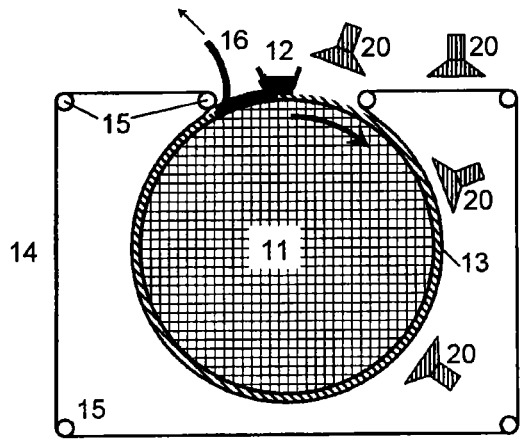
FIG. 2 shows a detail of a second embodiment of the inventive device for producing soft capsules.

The hot mixture was then processed by means of an inventive casting device to form a film. This device is illustrated in FIG. 1. It comprises a rotating heated drum (11), a spreader box (12), a revolving Teflon belt (14) and pulleys (15). The casting compound (13) is solidified to form a film (16).

Figure 3:
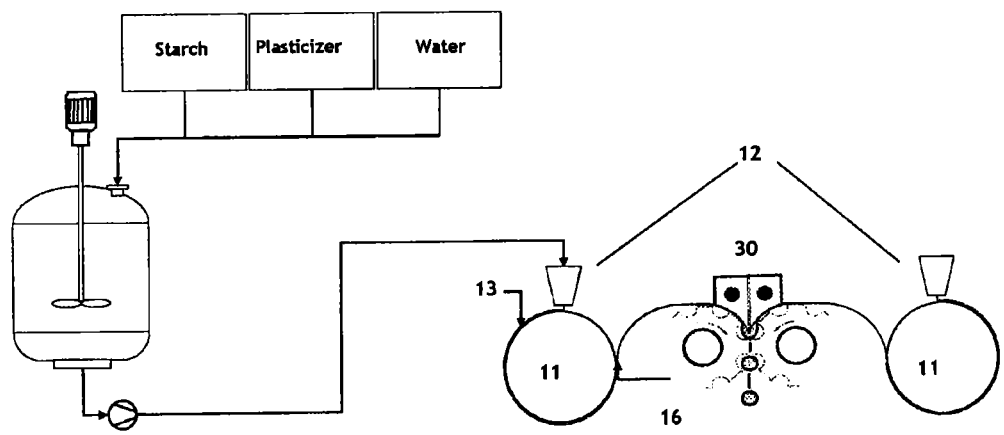
FIG. 3 shows an inventive device for producing soft capsules.

The drum (11) consists of a metal cylinder with a diameter of 50 cm which was heated to the temperature TZ of 105° C. by means of a heating fluid. The rotational speed n of the drum was 0.6 revolution per minute. The casting temperature TG of the mixture was 45° C. The mixture was cast to form a film (16) with a width of 25 cm and a thickness of 0.7 mm by means of the spreader box (12) on the rotating metal cylinder. The cast film (16) was covered by the corotating Teflon belt (14) over ¾ of the circumference, so that the water content in the film would remain constant. After a ¾ revolution, the film was detached from the metal cylinder and conveyed further to a rotary die device (30) of CS-J1-500R from Chang Sung, in which it was processed further at 2 rpm of the rotary dies to form soft capsules of the shape/size oval #10, filled with soy oil (see FIG. 3). The resulting soft capsules were completely transparent and the soft capsule halves could be welded together well; the fresh capsules had good dimensional stability and could be cleaned and dried well in a tumbler-drier. No birefringent starch grains were observed in the soft capsules. The mass temperature of the film on the drum after ¾ revolution was 91° C.

Figure 4:
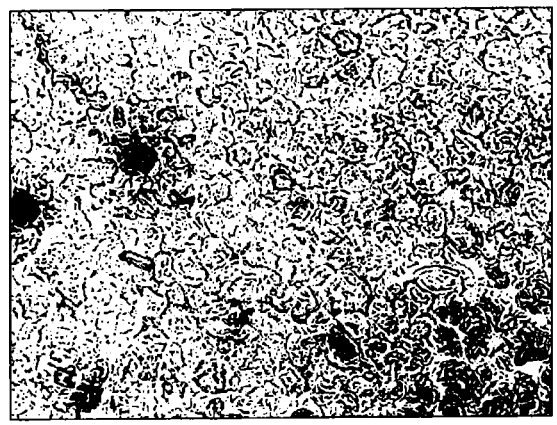
FIG. 4 shows a light microscopic image of an inventive starch film for producing a soft capsule according to Example 1, which was stored at a relative atmospheric humidity of 58%, with a magnification factor of 1:150 (a film detail with a width of 0.57 mm is shown).
Figure 5:
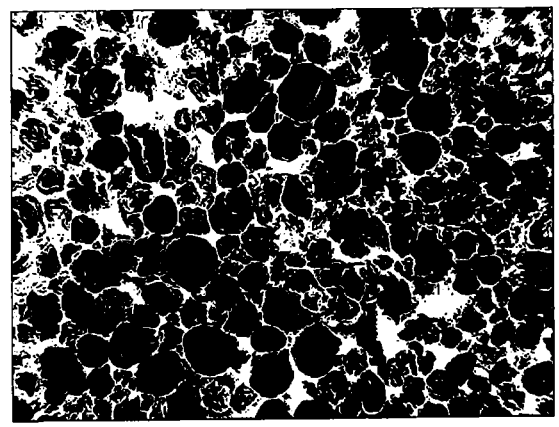
FIG. 5 shows a light microscopic image of an inventive starch film for producing a soft capsule according to Example 1 with a magnification factor of 150 (a film detail with a width of 0.57 mm is shown), which was stored at a relative atmospheric humidity of 58%.
Figure 6:
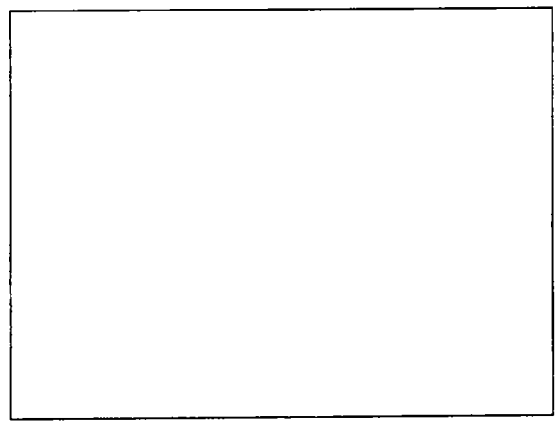
FIG. 6 shows a light microscopic image of an extruded starch film not according to the invention for producing a soft capsule according to EP 1 103 254 B1 with a magnification factor of 150 (a film detail with a width of 0.57 mm is shown).

A light microscopic image of a starch film which was stored over sodium bromide for 7 months (relative atmospheric humidity 58%) is shown in FIG. 4. This shows clearly that the film consists of interconnected starch grains. FIG. 5 shows a light microscopic image of a starch film which was stored for 7 months over magnesium chloride (relative atmospheric humidity 33%). An extruded starch film according to European Patent EP 1 103 254 B1 is shown in FIG. 6 for comparison. All the starch particles were destroyed by extrusion, so they can no longer be detected in the light microscope.

The modulus of elasticity values of films from Example 1, which were stored for 2 weeks at relative atmospheric humidities of 33%, 43%, 57% and 75%, were 23 MPa, 3.4 MPa, 3.7 MPa and 3.3 MPa, whereas the modulus of elasticity values of films having the same composition but produced by extrusion in the longitudinal direction and at the same atmospheric humidities were 4.5 MPa, 0.7 MPa, 0.9 MPa and 0.4 MPa.

Example 1a

Example 1 was repeated. The extruded starch S1E and the granular starch were mixed together with the mixture of water and plasticizer. It was found that the sequence in preparation of the casting mixture had no effect on further processing or product properties.

Example 1b

Example 1 was repeated. The finished casting mixture was stored for two hours at room temperature before further processing without having any effect on the further processing or the product property.

Example 1c

Example 1 was repeated. The finished casting mixture was stored for two hours at 45° C. before further processing without having any effect on further processing or the product property.

Example 2

Like Example 1, but instead of 38% water the casting compound had a water content of 35%. The temperature of the drum was set at 108° C. The mass temperature of the film on the drum after ¾ revolution was 93° C.

Example 3

Like Example 1, but instead of 38% water, the casting compound had a water content of 41.1%. The temperature of the drum was set at 103° C. The mass temperature of the film on the drum was 89° C. at ¾ revolution.

Example 4

Like Example 1, but the amount of extruded starch S1E in the casting compound was increased from 2.28% to 4.49% so that the dynamic viscosity at 45° C. and a shear rate of 1.1/s increased from 5.7 Pas to 21 Pas. The temperature of the drum was set at 105° C. The mass temperature of the film on the drum was approximately 90° C. at ¾ revolution.

Example 5

Like Example 1, but the hydroxypropylated crosslinked tapioca starch S1 was replaced by the native tapioca starch S2, and the starch S1E was replaced by the pregelatinized starch S2P. The temperature of the drum was set at 111° C. The mass temperature of the film on the drum after ¾ revolution was approximately 96° C.

Figure 13:
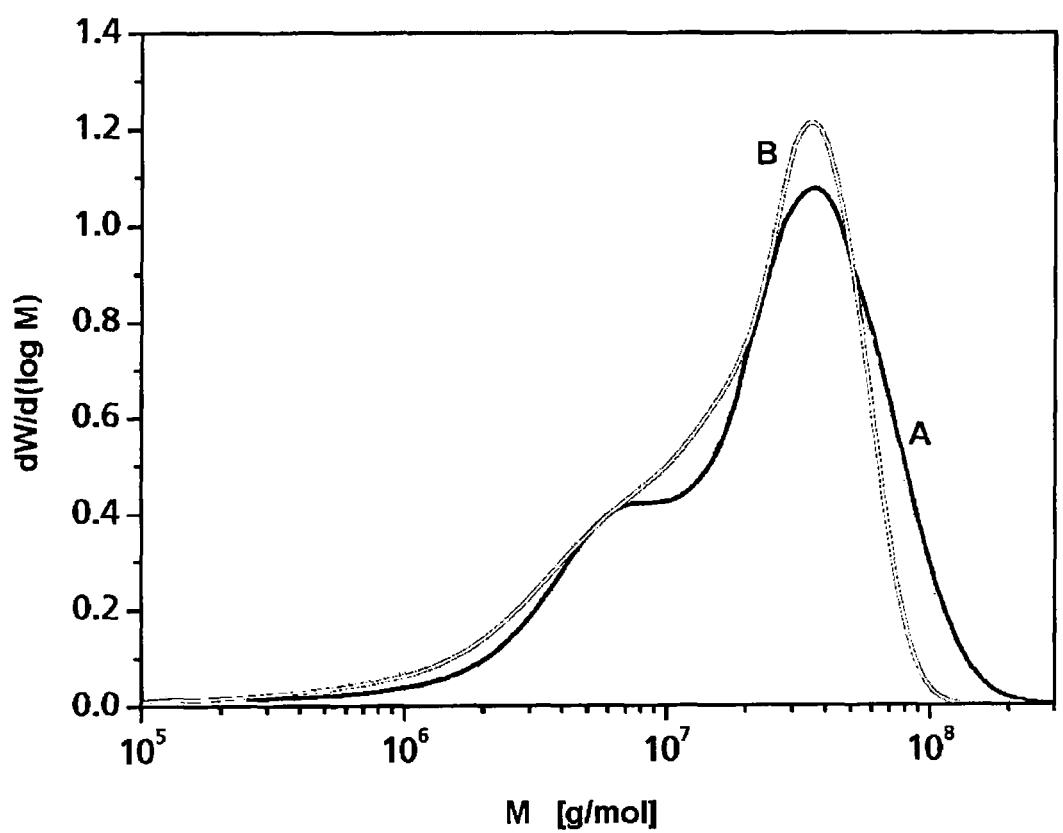
FIG. 13 shows the molar-mass distributions of a starting starch and a starch which was recovered by dissolving an inventive soft capsule according to Example 5 which was produced from this starting starch.

Before processing, the starches S2 and S2P had a weight-average molecular weight $M_w$ of 22,690,000 g/mol and the starch extracted from the soft capsules produced therewith had a molecular weight $M_w$ of 21,340,000, i.e., the molecular weight was only minimally reduced in production of the soft capsules (cf. FIG. 13).

Example 6

Like Example 1, but the glycerol content was increased. The temperature of the drum was set at 102° C. The temperature of the film after ¾ revolution was 88° C.

Example 7

Like Example 1, but the hydroxypropylated crosslinked tapioca starch S1 was replaced by the native waxy potato starch S4. The temperature of the casting mixture was 40° C. The temperature of the drum was set at 102° C. The temperature of the film after ¾ revolution was 87° C.

Example 8

Like Example 1, but the hydroxypropylated crosslinked tapioca starch S1 was replaced by the hydroxypropylated potato starch S5, and the starch S1E was replaced by the pregelatinized hydroxypropylated potato starch S5P. The temperature of the casting mixture was 40° C. The temperature of the drum was set at 101° C. The temperature of the film after ¾ revolution was 86° C.

The starches S5 and S5P had a weight-average molecular weight $M_w$ of 13,530,000 g/mol before processing and the starch extracted from the soft capsules produced therewith had a molecular weight $M_w$ of 13,490,000 at a first measurement, 15,460,000 at a second measurement, i.e., the molecular weight underwent practically no change in production of the soft capsules. The apparent increase in molecular weight in the second measurement could be attributed to the fact that the accuracy of molecular weight measurements is limited at these high molecular weights.

Example 9

Like Example 1, but the extruded starch S1E was replaced by the pregelatinized starch S1P.

The starches S1 and S1P have a weight-average molecular weight $M_w$ of 30,100,000 g/mol. The molecular weight analysis of the starch in the corresponding soft capsules revealed a molecular weight $M_w$ of 21,340,000 g/mol in a first measurement and a molecular weight $M_w$ of 20,220,000 g/mol in a second measurement, i.e., the molecular weight was reduced only slightly by the process. In particular in comparison with the extrusion method where the starch S1 had a molecular weight $M_w$ of only 920,000 g/mol, although it was extruded under the gentlest possible conditions, i.e., at a high water content and low shear rates.

Example 9a

Example 9 was repeated. But, the extruded starch S1E was replaced by the starch S1 (as dissolved starch) and after adding this starch S1 to the mixture of water and plasticizer, this starch S1 was destructured in this mixture by heating to 90° C. After subsequent cooling to a temperature below 45° C., the granular starch S1 was then added (as granular starch). This had no effect on the following process and the product properties.

Example 9b

Example 9a was repeated. To avoid cooling, the method was simplified by destructuring the starch S1 (as dissolved starch) in only a portion of the water-plasticizer mixture and then adding the rest of water and plasticizer at room temperature to lower the temperature to below 45° C.

Example 10

Like Example 9. But the pregelatinized starch SIP was replaced by the pregelatinized starch S6P. Here again, the same procedures could be used as those described in Examples 9a and 9b in order to destructure the starch S6 (as dissolved starch).

Examples 11 to 13

Like Example 1. But in these examples, the dissolved starch S1E was replaced by thickeners V1, V2 and V3, so that the disintegration behavior of the starch soft capsules in an acid aqueous medium could be accelerated. To dissolve the thickeners V2 (xanthan gum) and V3 (locust bean gum) in the mixture of water and plasticizer, the mixture of water, plasticizer and polysaccharide was heated to 90° C. as in Example 9a and was then cooled to a temperature below approximately 45° C. before adding the granular starch. Here again, the same variant can be used as in Example 9b to prevent active cooling of the mixture of water, plasticizer and dissolved polysaccharide.

Examples 14 to 16

Like Example 1. But in these examples, the dissolved starch S1E was replaced by various tapioca dextrins S7, S8 and S9, so that the disintegration behavior of the starch soft capsules in an acid aqueous medium could be accelerated. To dissolve the dextrins S7 and S8 in the mixture of water and plasticizer, the mixture of water, plasticizer and polysaccharide was heated to 90° C. according to Example 9a and then cooled to a temperature below approximately 45° C. before adding the granular starch (starch 1 according to Table 1). Here again, the same variant can be used as in Example 9b to prevent active cooling of the mixture of water, plasticizer and starch.

Example 17

With all the starch soft capsules obtained from Examples 1 through 17, the original starch particles could be recovered by placing them in water and visualized under a microscope by staining using Lugol's solution.

Figure 7:
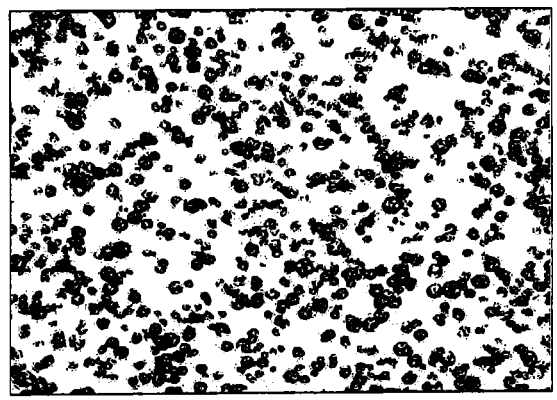
FIG. 7 shows a light microscopic image of an aqueous suspension of unprocessed, birefringent hydroxypropylated tapioca starch with a magnification factor of 150 (a detail with a width of 0.57 mm is shown).

A light microscopic image of the unprocessed granular tapioca starch S1 from Example 1 is shown in FIG. 7.

Figure 8:
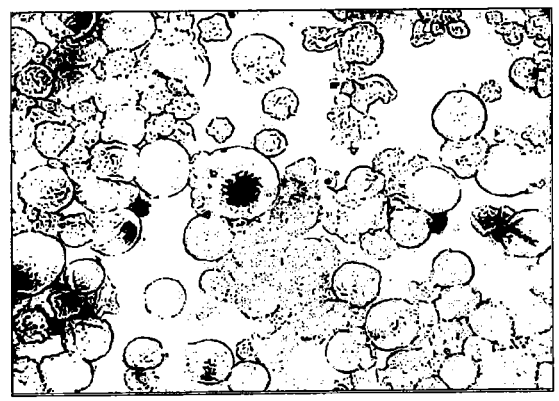
FIG. 8 shows a light microscopic image of an aqueous suspension of hydroxypropylated tapioca starch heated to 70° C., with a magnification factor of 150 (a detail with a width of 0.57 mm is shown).

FIG. 8 shows the change in this starch under the influence of temperature. The sample was prepared by suspending 20 weight percent starch in water in a test tube and heating for 5 minutes at 70° C. in a water bath. After cooling to room temperature, the starch was stained with iodine and examined under a microscope. Although FIG. 7 shows small birefringent starch particles, it can be seen that the particles in FIG. 8 are swollen and no longer show any birefringence.

Figure 9:
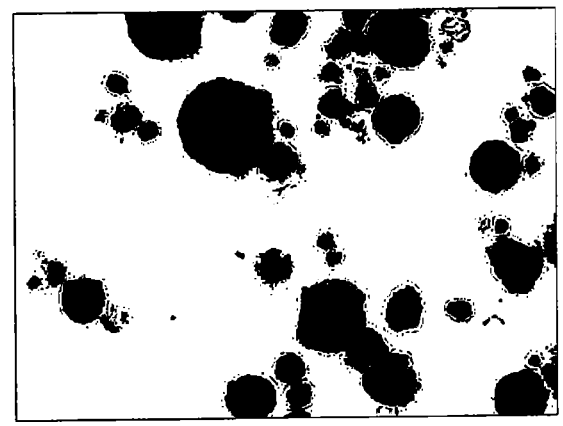
FIG. 9 shows a light microscopic image of an aqueous suspension of hydroxypropylated tapioca starch obtained by heating an inventive soft capsule according to Example 1 in water at 70° C., with a magnification factor of 150 (a detail with a width of 0.57 mm is shown).

FIG. 9 shows starch particles recovered from soft capsules. To do so, soft capsules from Example 1 were first stored for 7 months over magnesium chloride (relative atmospheric humidity: 33%). A sample was prepared by keeping approximately 100 mg of the soft capsule in 7 g water while stirring with a magnetic stirrer for 30 min at 70° C., whereupon the material disintegrated into particles. After cooling, a staining with iodine was performed. These starch particles from the film are stained more and are more dilute but do not differ significantly from those in FIG. 8 which were obtained by heating the suspended starch. It has thus been demonstrated that the soft capsule consists of destructured starch grains.

Example 18

Example 17 was repeated with the potato starch S5 and the soft capsules according to Example 8.

Figure 10:
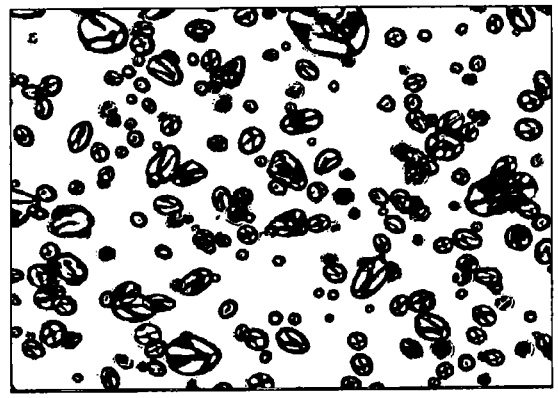
FIG. 10 shows a light microscopic image of an aqueous suspension of unprocessed hydroxypropylated potato starch under crossed polarizers, with a magnification factor of 150 (a detail with a width of 0.57 mm is shown).

A light microscopic image of the unprocessed starch S5 from Example 8 under crossed polarizers is shown in FIG. 10. The larger grains are a good illustration of the Maltese cross known to be typical of native starch.

Figure 11:
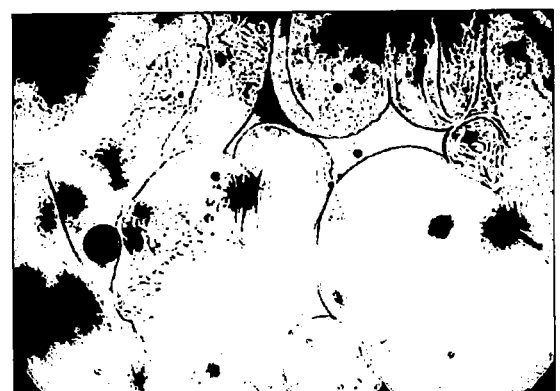
FIG. 11 shows a light microscopic image of an aqueous suspension of hydroxypropylated potato starch, heated to 70° C., with a magnification factor of 150 (a detail with a width of 0.57 mm is shown).
Figure 12:
FIG. 12 shows a light microscopic image of an aqueous suspension of hydroxypropylated potato starch, obtained by heating a sample of an inventive soft capsule according Example 5 in water at 70° C., with a magnification factor of 150 (a detail with a width of 0.57 mm is shown).

FIG. 11 shows the change in this starch after heating to 70° C. FIG. 12 shows starch particles recovered from soft capsules according to Example 8, stored 7 months over sodium bromide (relative atmospheric humidity: 58%).

They are like the starch grains in FIG. 11 but have stronger staining and are more dilute. This demonstrates that the soft capsule consists of destructured starch grains that can be converted to a suspension and can be recovered by sedimentation.

Example 19

FIG. 4 shows a light microscopic image of an inventive starch film for producing a soft capsule according to Example 1. A very thin layer of the starch film was sliced off with a razor blade and one drop of iodine solution was placed on it (the dark locations were stained more strongly). This preparation was then pressed by hand between two microscope slides to reduce the thickness of the film somewhat more. The resulting film thickness had approximately the thickness of two starch grains, so the grains were partially situated one above the other. Nevertheless it is readily discernible that the film consists of a dense packing of destructured starch grains (no more birefringence was discernible).

FIG. 5 shows a light microscopic image of an inventive starch film for producing a soft capsule according to Example 1. To visualize the individual starch grains more clearly in comparison with FIG. 4, the starch film obtained with the razor blade was swollen briefly at 70° C., the starch grains were stained with iodine and the film was pressed by hand between two microscope slides so that the film thickness corresponded approximately to the thickness of the grains. The grains are swollen due to the swelling at 70° C. and therefore are somewhat larger than those in FIG. 4.

Example 20

FIG. 6 shows a light microscopic image of an extruded starch film not according to the invention with a magnification factor of 150 (a film detail with a width of 0.57 mm is shown) for producing a soft capsule according to European Patent EP 1 103 254. Since the starch has dissolved completely, no more particles of starch are present. A mass content of approximately 1.5% of the dry film was obtained by recovery method 2, which could be sedimented from the solution and can be attributed to insoluble additives.

Example 21

The molar-mass distributions of the unprocessed starch S2 and the starch S2 that was processed to yield an inventive soft capsule according to Example 5 were compared with one another. To do so, the starch sample and/or the soft capsule sample was dissolved by pressure-cooking under defined conditions in a mini autoclave, and the molar-mass distribution of the molecularly dispersey dissolved starch was investigated by means of GPC-MALLS.

To do so, the starch samples were suspended in water with a concentration of 3 weight percent dry substance. This suspension was heated while stirring in a mini autoclave. After reaching 150° C., the temperature was maintained for 20 minutes. Next the solution was cooled to 60° C., diluted to 0.3 weight percent, filtered through a 5 μm membrane filter and measured on the GPC-MALLS.

The resulting molar-mass distributions are shown in FIG. 13, where A denotes the sample of the starting starch S2, and B denotes the soft capsule sample according to Example 5. The average molar-mass of the starting starch is found to be $M_w=22.69\times10^6$ g/mol and the molar-mass of the starch recovered from the soft capsule is found to be $M_w=21.84\times10^6$ g/mol. It can be ascertained that the relatively high molar-mass of the starting sample was not significantly degraded by processing to a soft capsule. Starting starch and processed starch were both in a comparable molar-mass range.

Measurement Methods

Dynamic viscosities were determined with the help of a Brookfield viscometer of the type LVDV-I+ at a shear rate of 1.1/s (5 rpm, spindle 25) and the stated temperatures.

The mechanical properties (elongation at break, modulus of elasticity) were measured on an Instron 5542 test system according to ISO 527.

Water contents were measured by drying over phosphorus pentoxide at 80° C. for 48 hours.

The GPC-MALLS was performed by means of an Alliance 2695 separation module from the company Waters, DRIDetector 2414 from the company Waters and a Dawn-HELEOS MALLS detector from Wyatt Technologie Inc., Santa Barbara, USA, at a wavelength 1=658 nm and a K5 flow-through cell. Columns: SUPREMA-Gel column set, exclusion limits S30000 with 108-106, S1000 with 2×106-5×104, S100 with 105-103. Eluent: DMSO with 0.09M $NaNO_3$, temperature: 70° C., analysis: Astra Software 5.3.0.18. A refractive index increment do/dc of 0.068 was taken for all samples.

The determination of the insoluble fraction in the film was performed as follows: first the dried soft capsules were stored for 2 months at 57% atmospheric humidity. A quantity of 100-150 mg (dry matter M0) in the form of a piece of film of the soft capsule shell of 0.5 mm thickness was swollen and/or dissolved together with 7 g demineralized water at 70° C. in a test tube for 30 min while stirring slowly with a magnetic stirrer. Then the test tube was centrifuged until the undissolved components had sedimented and the supernatant had become clear. The supernatant was then decanted. Next 7 g demineralized water was added and stirred with the sediment then centrifuged again and finally decanted. This procedure was repeated again to be sure that there were no longer any soluble constituents in the sediment. This sediment consisted of undissolved starch in the case of a film consisting of starch and plasticizer. Finally the sediment was dried for 48 hours at 80° C. over phosphorus pentaoxide and the dry mass (M1) were determined. The proportion of the mass that could be recovered after the dissolving process was thus obtained as 100×M1/M0 in weight percent. The proportion of starch that can be recovered after the dissolving process is obtained as follows for a starch film consisting of starch and plasticizer as 100×M1/(M0×(1−(WM/100))) in weight percent, where WM is the amount in weight percent of the plasticizer of the dry mixture. As a rule, the starch film still comprises at most minimal amounts of insoluble components, e.g., pigments (typically <0.5%) or fillers such as titanium dioxide (typically <1.5%) in addition to the starch particles. In case of need such components are subtracted from the dry matter M0 and the mass M1.

TABLE 1

| Example | Granular starch | Dissolved starch | Thickener | Granular starch [%] | Dissolved starch [%] | SCA [%] | Thickener [%] | H₂O [%] | WM [%] | Viscosity of the casting mixture [° C.] | Viscosity of the casting mixture [Pas] | Modulus of elasticity [MPa] | Elongation [%] | H₂O [%] | Wg. [%] |
|---|---|---|---|---|---|---|---|---|---|---|---|---|---|---|---|
| 1 | S1 | S1E | — | 38.97 | 2.28 | 0.25 | — | 38.0 | 20.5 | 45 | 5.7 | 0.03 | 386 | 36.5 | 86.3 |
| 2 | S1 | S1E | — | 40.85 | 2.39 | 0.27 | — | 35.0 | 21.5 | 45 | 14 | 0.04 | 430 | 34.2 | 87.2 |
| 3 | S1 | S1E | — | 37.06 | 2.17 | 0.24 | — | 41.1 | 19.5 | 45 | 2 | 0.02 | 531 | 40.0 | 86.7 |
| 4 | S1 | S1E | — | 36.54 | 4.49 | 0.50 | — | 38.0 | 20.5 | 45 | 21 | 0.03 | 420 | 37.0 | 82.3 |
| 5 | S2 | S2P | — | 38.97 | 2.28 | 0.25 | — | 38.0 | 20.5 | 45 | 2.8 | 0.03 | 452 | 36.8 | 92.1 |
| 6 | S1 | S1E | — | 39.08 | 2.29 | 0.25 | — | 33.5 | 24.9 | 45 | 21 | 0.02 | 510 | 33.1 | 91.5 |
| 7 | S4 | S1E | — | 38.98 | 2.28 | 0.25 | — | 38.0 | 20.4 | 40 | 8 | 0.14 | 148 | 35.8 | 73.4 |
| 8 | S5 | S5P | — | 39.42 | 1.88 | 0.21 | — | 38.0 | 20.5 | 40 | 4.3 | 0.03 | 430 | 36.5 | 64.2 |
| 9 | S1 | S1P | — | 39.43 | 2.09 | — | — | 38.0 | 20.5 | 45 | 11 | 0.04 | 421 | 36.7 | 88.4 |
| 10 | S1 | S6P | — | 39.45 | 2.09 | — | — | 38.0 | 20.5 | 45 | 4 | 0.02 | 523 | 34.3 | 79.5 |
| 11 | S1 | — | V1 | 41.11 | — | — | 0.41 | 38.0 | 20.5 | 45 | 35 | 0.05 | 440 | 37.9 | 89.2 |
| 12 | S1 | — | V2 | 41.32 | — | — | 0.21 | 38.0 | 20.5 | 45 | 17 | 0.04 | 508 | 37.7 | 91.2 |
| 13 | S1 | — | V3 | 41.11 | — | — | 0.41 | 38.0 | 20.5 | 45 | 20 | 0.04 | 467 | 37.8 | 92.5 |
| 14 | S1 | S7 | — | 33.24 | 8.30 | — | — | 38.0 | 20.5 | 45 | 13 | 0.03 | 507 | 37.2 | 88.4 |

TABLE 1-continued

| | | | | Recipe of the casting mixture | | | | | | Viscosity of the casting mixture | Fresh film | | | |
|---|---|---|---|---|---|---|---|---|---|---|---|---|---|---|
| Example | Granular starch | Dissolved starch | Thickener | Granular starch [%] | Dissolved starch [%] | SCA [%] | Thickener [%] | H$_2$O [%] | WM [%] | [° C.] [Pas] | Modulus of elasticity [MPa] | Elongation [%] | H$_2$O [%] | Wg. [%] |
| 15 | S1 | S8 | — | 33.23 | 8.30 | — | — | 38.0 | 20.5 | 45   10 | 0.02 | 563 | 37.4 | 86.2 |
| 16 | S1 | S9 | — | 36.56 | 5.02 | — | — | 38.0 | 20.5 | 45   22 | 0.02 | 499 | 35 | 84.7 |

Legend to Table 1
granular starch:
S1 hydroxypropylated crosslinked tapioca starch (Creamtex 75725 from Cerestar)
S2 native tapioca starch (from Cerestar)
S4 waxy potato starch (Eliane 100 from AVEBE)
S5 hydroxypropylated potato starch (Emden KH 15 from Emsland)
dissolved starch:
S1E starch S1, extruded, comprising 10% short-chain amylose
S1P starch S1, pregelatinized
S2P starch S2, pregelatinized
S5P starch S5, pregelatinized
S6P hydroxypropylated starch (Emcol H7 from Emsland), pregelatinized
S7 tapioca dextrin (Cleargum TA 90 from Roquette)
S8 tapioca dextrin (Tapioca Dextrin 11 from Tate&Lyle)
S9 mixture of 50% starch S1P and 50% tapioca dextrin (Dextrin D-400 from Cerestar)
Thickener:
V1 guar gum (Meypro Guar CSAA M-200 from Meyhall/Rhodia)
V2 xanthan gum (Keltrol HP E415 from Kelko)
V3 locust bean gum (Meypro LBG Fleur M-175 from Meyhall/Rhodia)
WM: glycerol as plasticizer
All percentage amounts are given in weight percent based on 100 weight percent of the total casting mixture.
The mechanical properties (modulus of elasticity and elongation) of the fresh film were measured at a temperature of 25° C., 10 min after producing the film.
Wg.: recovery according to recovery method no. 1

The invention claimed is:

1. A soft capsule shell comprising: a) 15 to 55 weight percent of plasticizer; b) >40 weight percent of starch subtracting the plasticizer; c) 0.1-25 weight percent of water of a total weight; d) up to 20 weight percent of thickener, after subtracting the plasticizer; and e) up to 10 weight percent of carrageenan or carrageenans, after subtracting the plasticizer;
wherein the starch of the soft capsule shell comprises at least 30 percent starch particles that are destructured, wherein the destructured starch particles are bonded to one another, wherein the destructured starch particles are insoluble in water and are recovered by sedimentation after dissolving the soft capsule shell in water for 30 min at 70 degrees Celsius, and wherein the starch of the soft capsule shell has a weight-average molecular weight of at least 2,500,000 g/mol.

2. The soft capsule shell of claim 1 wherein said soft capsule shell comprises a matrix of the destructured starch particles bonded to one another.

3. The soft capsule shell of claim 1 wherein the soft capsule has a proportion of at least 35 weight percent solids content, which are recovered after dissolving the soft capsule at 70 degrees Celsius by sedimentation.

4. The soft capsule shell of claim 1 comprising additives and adjuvants.

5. The soft capsule shell of claim 1 wherein the starch of the soft capsule shell has a weight-average molecular weight of at least 3,000,000 g/mol.

6. The soft capsule shell of claim 1 wherein the starch of the soft capsule shell has a weight-average molecular weight of at least 4,000,000 g/mol.

7. A soft capsule shell comprising: a) 15 to 55 weight percent of plasticizer; b) >40 weight percent of starch, after subtracting the plasticizer; c) 0.1-25 weight percent of water of a total weight of the soft capsule shell; d) up to 20 weight percent of thickener, after subtracting the plasticizer; and e) up to 10 weight percent of carrageenan or carrageenans, after subtracting the plasticizer;
wherein said starch of the soft capsule shell comprises starch particles that are destructured, wherein the destructured starch particles are bonded to one another, wherein the destructured starch particles are insoluble in water, wherein the amount of destructured starch particles recovered by sedimentation after dissolving the soft capsule shell in water for 30 min at 70 degrees Celsius, is at least 25% of the dry weight of the soft capsule shell, and wherein the starch of the soft capsule shell has a weight-average molecular weight of at least 2,500,000 g/mol.

* * * * *